US006537497B1

(12) United States Patent
Woodland

(10) Patent No.: US 6,537,497 B1
(45) Date of Patent: Mar. 25, 2003

(54) METHOD AND COMPOSITION FOR DETECTING IGNITABLE LIQUIDS

(76) Inventor: John H. Woodland, 901 N. C St., Indianola, IA (US) 50125

( * ) Notice: Subject to any disclaimer, the term of this patent is extended or adjusted under 35 U.S.C. 154(b) by 28 days.

(21) Appl. No.: 09/615,998

(22) Filed: Jul. 14, 2000

(51) Int. Cl.[7] .................. G01N 15/06; G01N 21/29; C09K 11/06; C08L 67/00
(52) U.S. Cl. .................. 422/68.1; 422/50; 422/69; 422/82.05; 422/119; 422/57; 252/301.16; 252/301.35; 252/408.1; 252/600; 524/845; 524/904; 524/914; 524/917; 524/923
(58) Field of Search .................. 422/50, 54, 57, 422/68.1, 69, 82.05, 901, 119, 292; 252/408.1, 600, 301.35, 301.16; 524/845, 904, 914, 917, 923

(56) References Cited

U.S. PATENT DOCUMENTS

| | | | |
|---|---|---|---|
| 2,800,460 A | | 7/1957 | Grosskopf |
| 4,780,518 A | | 10/1988 | Ceaser |
| 4,911,830 A | * | 3/1990 | Bromley et al. ....... 252/301.16 |
| 5,030,591 A | | 7/1991 | Cole |
| 5,057,434 A | * | 10/1991 | Prusik et al. .................. 436/2 |
| 5,094,777 A | * | 3/1992 | DiPietro ................. 252/301.35 |
| 5,979,226 A | * | 11/1999 | Cavestri et al. .............. 73/40.7 |

FOREIGN PATENT DOCUMENTS

| | | |
|---|---|---|
| GB | 2 116 710 A | 9/1983 |

OTHER PUBLICATIONS

Yun–Seng Giang, Wei–Tun Chang, Chen–Then Wang and Chin–Wang Huang, "A Basic Study of the Properties of Accelerants in Fire Residence for Better Sampling in Arson Analysis", Central Police University, Taiwan, Republic of China and Chung Yuan Christian University, Taiwan, Republic of China; pp. 259–262.

Furton, et al., "Application of solid–phase microextraction to the recovery of explosives and ignitable liquid residues from forensic specimens", Journal of Chromatography A, 885 (2000), pp. 427–432.

* cited by examiner

*Primary Examiner*—Robert J. Warden, Sr.
*Assistant Examiner*—Monzer R. Chorbaji
(74) *Attorney, Agent, or Firm*—McKee, Voorhees & Sease, P.L.C.

(57) ABSTRACT

The invention discloses a composition and method of absorbing and/or detecting the presence of ignitable liquids. The composition includes a hydrophobic polymer, a hydrophobic long-chain carboxylic acid and, optionally, a hydrophobic solvent indicator dye and a hydrophobic white metallic oxide. The composition may be applied to an area suspected of containing an ignitable liquid and allowed to remain on the area for a time period sufficient to react with the ignitable liquid. If an ignitable liquid is present, the composition will form an aggregate by agglomeration with the ignitable liquid.

20 Claims, No Drawings

METHOD AND COMPOSITION FOR DETECTING IGNITABLE LIQUIDS

BACKGROUND OF THE INVENTION

Arson is a costly public safety problem. The cost of fire damage in the United States is several billions of dollars per year. Arson, the willful and malicious burning of property, accounts for approximately one third of these costs.

The most effective way to try and reduce the cost and damage caused by fire is through the use of effective fire investigation to find and prosecute those responsible. However, the devastation, charred debris, collapsed structures, water-soaked ashes, weather conditions, together with the smoke and stench makes arson extremely difficult to detect and prove.

The basic role of a fire investigator is twofold: first to determine the origin of the fire, and second to examine the site of the fire to determine what caused the fire to start. Once the origin of the fire is found, examination of the debris is necessary to determine the fire's cause. A major objective in any suspected case of arson is to search for, locate, sample and analyze residual accelerants, which are usually in the form of ignitable liquids.

Most purposefully caused fires involve the use of an accelerant to speed the ignition and rate of spread of the fire. The most commonly used accelerants are diesel fuel, mineral spirits, kerosene, gasoline, and turpentine due to their flammability and ready availability. Less commonly used accelerants include alcohols, ketones, and industrial solvents. The amount of accelerant remaining after a fire depends not only on factors such as quantity and type of compound used, but also on the nature of material it is poured on, the elapsed time since the fire, and the severity of the fire.

There are currently several methods for detecting accelerants available. First, physical indicators, such as localized burn patterns to floors and surfaces and overhead damage inconsistent with the naturally available fuel, can be used to detect the presence of accelerants. The primary problem with physical indicators is that they are frequently destroyed during the course of the fire. Further, physical evidence which indicates a hot and intense fire, such as a color change or spalling in concrete, melted aluminum or brass and deformation of steel, are unreliable as indicators of the presence of an accelerant, as many combustible materials tend to burn with the same intensity as accelerants.

Fire investigators often rely upon their own sense of smell to attempt to identify the presence of accelerants. As would be expected, this ability varies greatly amongst investigators since, like most other senses, it can become highly developed through experience, or permanently impaired. In addition, continual smelling of the toxic vapors produced by accelerants cause the sense of smell to become less effective, and lessens the ability of the investigator to discriminate between accelerant vapors.

Sniffer dogs are also used for the detection of accelerants. Dogs have a keener sense of smell than humans, and also have much greater ability to discriminate between target scents. However, the effectiveness of sniffer dogs is entirely dependent on the level of training the dog has been given. Moreover, dogs are sometimes unable to detect odorless fire accelerants, because the accelerant molecule is not aromatic.

Portable hydrocarbon detectors are commonly used in accelerant detection at fire scenes. Hydrocarbon detectors are extremely sensitive and able to separate and detect trace amounts of volatile hydrocarbons. The extreme sensitivity of a hydrocarbon detector is also its biggest drawback, however, since it is associated with a large number of false positives. For instance, a portable hydrocarbon detector can detect hydrocarbons from various materials such as rubber-backed carpet, carpet and tile glue, or burnt plastic, and the results are wrongly interpreted as indicating the presence of an ignitable liquid used as an accelerant.

It is therefore an object of the present invention to provide a more accurate method and means of detecting arson by detecting the presence of ignitable liquids.

It is a further object of the present invention to provide a method and means of absorbing crude oil, petroleum distillates, and solvents to prevent absorption of these substances into the environment.

It is yet another object of the present invention to provide a method and means of detecting and/or absorbing ignitable liquids which is sensitive, yet does not result in a high incidence of false positives.

It is another object of the present invention to provide a method and means of detecting and/or absorbing ignitable liquids which does not rely on the subjective nature of a person or animal's sense of smell.

It is still another object of the present invention to provide a method and means of detecting and/or absorbing ignitable liquids which is economical and easy to use.

Other objects of the invention will become apparent from the description of the invention which follows.

SUMMARY OF THE INVENTION

The present invention relates to the use of a chemical composition for detecting and/or absorbing ignitable liquids using an ignitable liquid absorbent (ILA). The ILA includes a hydrophobic polymer as a primary absorbent and a hydrophobic long-chain carboxylic acid. The ILA may also contain a hydrophobic solvent indicator dye and a hydrophobic white metallic oxide.

The ILA may be applied to an area suspected of containing an ignitable liquid. If the ILA comes in contact with an ignitable liquid, it changes in form from a powder to an aggregate by means of agglomeration. If a hydrophobic solvent indicator dye is included in the ILA, the aggregate also changes color, thereby more precisely indicating the location of an ignitable liquid. Evidence samples taken using the absorbent can then be tested using conventional laboratory procedures, such as gas chromatography or mass spectroscopy to determine the presence of target liquid accelerants or ignitable liquids.

DETAILED DESCRIPTION OF THE INVENTION

The present invention is based on an improved method and means for detecting ignitable liquids.

Through education, training, and experience, fire investigators are able to investigate a fire scene and, based on burn patterns and other evidence collected from the scene, form an expert opinion as to the origin and cause of the fire. However, on many fire scenes where the fire has been intentionally ignited, the use of an ignitable liquid as a fire accelerant is not always obvious, because it remains only in trace amounts after the fire. The remaining trace amounts of ignitable liquid may also be semi- or fully soluble in water, thereby becoming even further diluted as a result of fire suppression efforts prior to the investigation.

Using the composition of the present invention, even trace amounts of the ignitable liquid used to accelerate the fire can be identified and collected as evidence. Further, fuels that are soluble in water can be separated from the water, identified, and collected as evidence.

The first ingredient in the ignitable liquid absorbent (ILA) of this invention is a hydrophobic polymer powder or micro-fiber. Polymers which meet this definition are capable of absorbing or adsorbing ignitable liquids, such as alcohols, ketones, crude oil, petroleum distillates, or solvents. Ignitable liquids are typically nonpolar, or have limited polarity so as not to strongly hydrogen bond with water molecules. Because the water molecule is highly polar, the majority of ignitable liquids will not form a homogenous solution with water, but will instead form an identifiable two-phase liquid separation. Some ignitable liquids, such as specific alcohols or ketones with the lowest molecular weight of their class, will form a homogenous solution when introduced in water. The ILA of this invention has the capability of absorbing these liquids without absorbing a significant amount of water, thus causing their separation from water.

Hydrophobic polymers for use in this invention are generally composed of long linear carbon chains or cross-linked carbon chains and may have an oxygen, sulfur, nitrogen, or halon molecule substituent. Preferred hydrophobic polymers include polypropylene, polyethylene, polybutylene, polystyrene, polyurethane, polyisocyanurate, polyvinyl acetate, polyvinyl chloride, polyethylene terephthalate, polymerized acrylonitrile butadiene styrene, and hydrophobic zeolites or dendrimers. The most preferred hydrophobic polymer is polypropylene. The hydrophobic polymer should be included in the composition in an amount ranging from about 0.1–99% by weight, with about 60–90% by weight being preferred, and about 70–80% by weight being most preferred.

The next ingredient in the ILA is a long-chain carboxylic acid or derivative thereof that dissolves or softens in ignitable liquids but remains hydrophobic after dissolving. Examples of such compounds include octadecanoic acid (stearic acid), octadecanamide (stearamide), octadecyl acetate, ethyl chloroacetate, and acetyl bromide. The most preferred long-chain carboxylic acid is stearic acid. The long-chain carboxylic acid serves as a primary binder and hydrophobic barrier in the ILA. The long-chain carboxylic acid should be included in the ILA in an amount ranging from about 1–99% by weight, with about 10–40% by weight being preferred, and about 10–25% by weight being most preferred.

The ILA may also include a hydrophobic indicator dye to more precisely ascertain the presence and location of an ignitable liquid. Such dyes are well known in the art and are commonly referred to as "solvent dyes." Several companies, such as Neha-Chem, Max-Pages, Tri Chem Inc., Neomark International Corp. and Chekemcolour Limited, manufacture solvent dyes. Hydrophobic solvent indicator dyes are generally soluble and/or miscible in a wide range of organic solvents, and in synthetic and natural resins. Hydrophobic solvent indicator dyes generally consist of metal complex dyes (e.g. chrome-complex and cobalt-complex), anthraquinone dyes, dye salt, and azo dyes.

Any hydrophobic solvent indicator dye may be used in the ILA of this invention, including Solvent Blue (e.g. #4, 24, 35, 36, 38, 70, 78, 122), Solvent Red (e.g. #8, 23, 24, 25, 49, 52, 109, 111, 122, 130, 132, 135, 146, 149, 168, 169, 179, 196, 197), Vat Red 41, Solvent Violet (e.g. #8, 9, 11, 13, 28, 31, 59, 132), Solvent Blue (e.g. #4, 35, 36, 38, 70, 78, 122), Solvent Black (e.g. #27, 29, 34, 45, 46), Solvent Yellow (e.g. #2, 14, 16, 19, 21, 33, 45, 56, 72, 82, 93, 98, 114, 145, 163, 176), Solvent Orange (e.g. #45, 54, 60, 62, 63, 86), Solvent Green (e.g. #3, 5), and Solvent Brown (e.g. #43). A preferred hydrophobic indicator dye for use in this invention is Solvent Blue (e.g. #36).

The hydrophobic indicator dye serves to indicate when the ILA of this invention comes into contact with an ignitable liquid. The hydrophobic indicator dye should be included in the ILA in an amount ranging from about $1 \times 10^{-6}$ to about 99% by weight, with about 0.02 to 3% by weight being preferred, and about 0.03% to 1% by weight being most preferred.

The ILA of this invention also preferably includes a hydrophobic white metallic oxide, which serves as a contrast agent for the hydrophobic solvent indicator dye. Specifically, the hydrophobic white metallic oxide provides a white background to increase the visibility of the dye when it changes color to indicate the presence of an ignitable liquid. Hydrophobic white metallic oxides include aluminum oxide, titanium dioxide, and zinc oxide. Titanium dioxide is preferred. If included in the ILA, the hydrophobic white metallic oxide should be present in a concentration ranging from about 0.1–99% by weight, with about 7–22% by weight being preferred, and about 9–14% by weight being most preferred.

In manufacturing the ILA of this invention, the long-chain carboxylic acid is first heated to a temperature of at least 69.3° C. in order to melt, but not boil, the long-chain carboxylic acid. Once melted, the hydrophobic polymer is added and blended to form a homogenous mixture. If included in the ILA, the hydrophobic white metallic oxide should be added at the same time as the hydrophobic polymer. In the alternative, the hydrophobic polymer may be purchased as a mixture with the white metallic oxide, and the combination added all at once to the melted long-chain carboxylic acid.

Once formed, the homogenous mixture is cooled to ambient temperature, and ground to form a fine powder. If included in the ILA, the indicator dye powder is mixed in at this time. The powder preferably has a particle size of less than about 30 microns, with between 5 microns to 25 microns being most preferred. Powders having a larger particle size will work in the invention. However, smaller particle sizes are preferred since they increase the surface area of ILA exposed to the ignitable liquid.

The resulting powdered ILA should be stored in a dry, clean container until ready for use. If it is intended to be used in conjunction with an arson investigation, the ILA is preferably stored in a nylon evidence bag or other non-contaminated container.

In practice, the ILA of this invention may be applied by sprinkling or other means on an area suspected of containing an ignitable liquid. The amount of ILA used for this purpose will vary according to the degree of sensitivity desired in the testing procedure. As a general rule, the ILA may be applied to the testing area in an amount of about 0.5 kilograms/9 square meters.

The ILA should remain on the testing area for an amount of time sufficient for the ILA to react with the ignitable liquid and form an aggregate and/or for an amount of time sufficient to allow the hydrophobic indicator dye to change color. This time frame will vary depending on a number of factors, including the amount of ignitable liquid present, the amount of ILA added, and the temperature of the test site, with the speed of the test increasing proportionately as the temperature increases. For instance, if the conditions of the test site are fairly warm (such as would be the case during summer months), the ILA may react to the presence of ignitable liquid in as little as ten seconds. Even during cooler testing conditions, however, and if an ignitable liquid is present at the test scene, the ILA will typically indicate its presence within fifteen minutes, in levels at least as low as 0.1 ppm, which are not perceptible to the human senses. If the ILA comes into contact with an ignitable liquid, it will not only change in color, but in texture. Specifically, the powdered ILA will change from a powder to an aggregate by agglomeration.

Once the testing is complete, and if desired and/or required by law, samples from the area testing positive for ignitable liquid may be collected and chemically tested in a laboratory or by other conventional means, such as gas chromatography or mass spectroscopy, to specifically identify the types and brands of the ignitable liquids present in the samples.

It is specifically contemplated that the ILA and methods of this invention may be used for the general purpose of detecting the presence of ignitable liquids not only for purposes of arson investigation, but in any situation where it is desired to detect and/or absorb such compounds.

For example, the ILA of this invention can be used as an absorbent for hazardous materials in clean-up methods. Further, the ILA of this invention can be used as a barrier for preventing crude oil, petroleum distillates, and solvents from contacting a shoreline or other environmentally sensitive areas following a spill. The ILA is especially effective for this purpose since, upon reaction with the ignitable liquid, the ILA forms an aggregate by agglomeration which serves as a barrier that does not break apart even upon exposure to external forces such as wave action, high winds, etc. This is in stark contrast to prior art clean-up compositions which merely aggregate to form loosely connected clumps that break apart once exposed to these external forces.

In this respect, the ILA can be delivered to the site of the spill by means of aerial dispersal, from sea level or ground level. In the case of a marine crude oil spill, the ILA preferably includes a brightly-colored indicator dye, such as fluorescent orange, to maximize the potential for tracking the spill from satellite or at sea level. The ILA can be safely used in marine and freshwater environments without presenting an additional environmental hazard.

In addition, the ILA can be mixed with an aggregate, or used alone, and packed around underground fuel storage tanks or delivery lines to prevent and/or minimize fuel leaks from entering the surrounding ground and groundwater. The ILA can also be used to remove specific solvents from surface water, ground water, or municipal water systems. Moreover, the ILA may be used to absorb alcohol from water without the addition of heat, thus reducing the cost of alcohol distillation.

The following examples are offered to illustrate but not limit the invention. Thus, they are presented with the understanding that various formulation modifications as well as method of delivery modifications may be made and still be within the spirit of the invention.

EXAMPLE 1

Manufacture of Ignitable Liquid Absorbent 1.5 grams of stearic acid were placed in a 50 ml beaker and heated on a hotplate to a melting point of 69.3° C. While continuously heating and stirring, 4.5 grams of 5-micron polypropylene powder were added until the polypropylene powder was evenly coated with stearic acid.

The mixture was removed from the hotplate and allowed to cool to room temperature. The mixture was ground and screened to obtain a particle size of approximately 10-microns. Approximately 0.02 grams of powdered hydrophobic solvent indicator dye were added to the screened mixture and stirred until the mixture became an even off-white color to form an ignitable liquid absorbent (ILA).

EXAMPLE 2

Reaction of ILA with Ignitable Liquids

Materials and Methods

Four, 5 ml beakers containing 3 ml of water were prepared. To one beaker, approximately 1 gram of the ILA manufactured in Example 1 was added. The ILA remained in powdered form and floated on the water with no indication of a reaction.

To the second 5 ml beaker containing 3 ml of water, 1 ml of ethyl alcohol was added and stirred. To this beaker, approximately 1 gram of the ILA was added. A reaction occurred changing the appearance of the ILA from an off-white color to a light blue within several seconds. Agglomeration also occurred with particle sizes ranging from approximately 10 to 25 micron size, which formed a seal over the top of the water. The water became slightly cloudy.

To the third 5 ml beaker containing 3 ml of water, 1 ml of acetone was added and stirred. To this beaker, approximately 1 gram of the ILA was added. A reaction occurred changing the appearance of the ILA from an off-white color to a medium blue within several seconds. Agglomeration occurred with particle sizes ranging from approximately 10–25 micron size, which formed a seal over the top of the water.

To the fourth 5 ml beaker containing 3 ml of water, 1 ml of a medium petroleum distillate was added. Stirring was not required. To this beaker, approximately 1 gram of the ILA was added. A reaction occurred changing the appearance of the ILA from an off-white color to a dark blue immediately. All of the petroleum distillate was absorbed into the mixture. Agglomeration occurred with particle sizes ranging from approximately 10 to 25 micron size, which formed a seal over the top of the water.

In the second part of the experiment, 2 ml each of the medium petroleum distillate, acetone, and ethyl alcohol were poured onto a worn concrete surface at separate locations. The ignitable liquids were allowed to stand until absorption into the concrete was complete.

Approximately 1 gram of the ILA was poured on top of the areas of the concrete that had absorbed the ignitable liquids. In each case, the ILA absorbed the ignitable liquid from the concrete and reacted with a slightly more intense color than the first part of this experiment, but at a slower rate.

DISCUSSION

The absorbent mixture is hydrophobic and has a lower density than water, thus causing it to float on water. In water, each of the selected ignitable liquids reacted with the ILA as theorized. The medium petroleum distillate had the strongest and fastest reaction. Acetone had the second strongest reaction. Ethyl alcohol reacted the least by comparison, but the reaction was still significant. The alcohol and water solution became cloudy, most probably because some alcohol remained in solution and dissolved the stearic acid, which separated from the absorbent mixture.

The absorption of the ignitable liquids from concrete resulted in a significant reaction with the medium petroleum distillate having the greatest reaction. With the elimination of water, the absorption of acetone and ethyl alcohol is observably more intense but at a slower rate, as compared to the first part of the experiment.

What is claimed is:

1. A method of absorbing and/or detecting one or more ignitable liquids comprising:

applying a composition comprising a hydrophobic polymer, a hydrophobic solvent indicator dye, a hydrophobic white metallic oxide, and a hydrophobic long-chain carboxylic acid to an area suspected of containing one or more ignitable liquids; and allowing the composition to remain on the area for a period of time sufficient for the composition to react and form an aggregate with one or more of the ignitable liquids.

2. A method according to claim 1 whereby the composition is allowed to remain on the area for a time period of no more than about 15 minutes.

3. A method according to claim 1 whereby the composition is applied to the area in an amount of about 0.5 kilograms/9 square meters.

4. A method according to claim 1 wherein the composition is applied to an ignitable liquid selected from the group consisting of crude oil, petroleum distillates, diesel fuel, kerosene, mineral spirits, turpentine, gasoline, alcohols, ketones, and industrial solvents.

5. A method of manufacturing a composition for detecting the presence of one or more ignitable liquids comprising:

heating a hydrophobic long-chain carboxylic acid at a temperature sufficient to melt but not boil the hydrophobic long-chain carboxylic acid;

adding the hydrophobic polymer to the melted hydrophobic long-chain carboxylic acid to form a homogenous mixture;

cooling the homogenous mixture to ambient temperature;

grinding the cooled homogenous mixture to form a powder; and mixing a hydrophobic indicator dye into the powder.

6. A method according to claim 5 whereby a hydrophobic white metallic oxide is added along with the hydrophobic polymer to form the homogenous mixture.

7. A method according to claim 5 whereby the cooled homogenous mixture is ground to a particle size of less than about 30 microns.

8. A composition for absorbing and/or determining the presence of an ignitable liquid comprising:

about 60–90% by weight of a hydrophobic polymer;

about 10–40% by weight of a hydrophobic long-chain carboxylic acid;

about 0.02–3.0% by weight of a hydrophobic solvent indicator dye; and about 7–22% by weight of a hydrophobic white metallic oxide.

9. A composition according to claim 8, whereby the hydrophobic solvent indicator dye is selected from the group consisting of Solvent Blue, Solvent Red, Vat Red, Solvent Violet, Solvent Black, Solvent Yellow, Solvent Orange, Solvent Green, and Solvent Brown.

10. A composition according to claim 8, whereby the hydrophobic solvent indicator dye is present in an amount ranging from about 0.03%–1.0% by weight.

11. A composition according to claim 8, whereby the hydrophobic polymer is selected from the group consisting of polypropylene, polyethylene, polybutylene, polystyrene, polyurethane, polyisocyanurate, polyvinyl acetate, polyvinyl chloride, hydrophobic zeolites, and hydrophobic dendrimers.

12. A composition according to claim 8, whereby the hydrophobic polymer is present in an amount ranging from about 70–80% by weight.

13. A composition according to claim 8, whereby the hydrophobic long-chain carboxylic acid is selected from the group consisting of octadecanoic acid, octadecanamide, octadecyl acetate, ethyl chloroacetate, and acetyl bromide.

14. A composition according to claim 8, whereby the hydrophobic long-chain carboxylic acid is present in an amount ranging from about 10–25% by weight.

15. A composition according to claim 8, whereby the hydrophobic white metallic oxide is selected from the group consisting of aluminum oxide, titanium dioxide, and zinc oxide.

16. A composition according to claim 15 whereby the hydrophobic white metallic oxide is present in an amount ranging from about 9–14% by weight.

17. A composition according to claim 8 which is a fine powder having a particle size of less than about 30 microns.

18. A method of absorbing and/or detecting one or more ignitable liquids comprising:

applying a composition comprising about 60–90% by weight of a hydrophobic polymer, about 10–40% by weight of a hydrophobic long-chain carboxylic acid, about 0.02–3.0% by weight of a hydrophobic solvent indicator dye, and from about 7–22% by weight of a hydrophobic white metallic oxide to an area suspected of containing one or more ignitable liquids; and allowing the composition to remain on the area for a period of time sufficient for the composition to react and form an aggregate with one or more of the ignitable liquids.

19. A composition for absorbing and/or determining the presence of an ignitable liquid comprising:

about 60–90% by weight of a hydrophobic polymer;

about 10–40% by weight of a hydrophobic long-chain carboxylic acid;

about 0.02–3.0% by weight of a hydrophobic solvent indicator dye; and about 7–22% by weight of a hydrophobic white metallic oxide;

said composition being powdered.

20. A method of absorbing and/or detecting one or more ignitable liquids comprising:

applying a powdered composition comprising about 60–90% by weight of a hydrophobic polymer, about 10–40% by weight of a hydrophobic long-chain carboxylic acid, about 0.02–3.0% by weight of a hydrophobic solvent indicator dye, and from about 7–22% by weight of a hydrophobic white metallic oxide to an area suspected of containing one or more ignitable liquids; and allowing the composition to remain on the area for a period of time sufficient for the composition to react and form an aggregate with one or more of the ignitable liquids.

* * * * *